US009080606B2

(12) United States Patent
Kalenyak et al.

(10) Patent No.: US 9,080,606 B2
(45) Date of Patent: Jul. 14, 2015

(54) DEVICE FOR MOUNTING AND DRIVING A ROTATABLE PART OF A GANTRY OF A COMPUTER TOMOGRAPHY UNIT AND COMPUTER TOMOGRAPHY UNIT

(75) Inventors: Johann Kalenyak, Schesslitz (DE); Hans-Jürgen Müller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 389 days.

(21) Appl. No.: 13/639,064

(22) PCT Filed: Mar. 22, 2011

(86) PCT No.: PCT/EP2011/054334
§ 371 (c)(1),
(2), (4) Date: Oct. 2, 2012

(87) PCT Pub. No.: WO2011/128187
PCT Pub. Date: Oct. 20, 2011

(65) Prior Publication Data
US 2013/0028389 A1   Jan. 31, 2013

(30) Foreign Application Priority Data

Apr. 15, 2010   (DE) .......................... 10 2010 015 061

(51) Int. Cl.
*A61B 6/03*   (2006.01)
*F16C 32/04*   (2006.01)
*A61B 6/00*   (2006.01)
*H02K 7/09*   (2006.01)

(52) U.S. Cl.
CPC ............. *F16C 32/0493* (2013.01); *A61B 6/035* (2013.01); *A61B 6/4441* (2013.01); *A61B 6/56* (2013.01); *H02K 7/09* (2013.01); *F16C 2300/14* (2013.01); *F16C 2316/10* (2013.01); *H02K 2213/12* (2013.01)

(58) Field of Classification Search
CPC ............. A61B 6/035; A61B 6/56; H02K 7/09
USPC ........................................ 378/4, 15
See application file for complete search history.

(56) References Cited

U.S. PATENT DOCUMENTS 4,723,259 A * 2/1988 Amor et al. ..................... 378/10
5,438,605 A * 8/1995 Burke et al. ................... 378/135
5,467,244 A   11/1995 Jayawant et al.

(Continued)

FOREIGN PATENT DOCUMENTS

EP          0549912 A1 *  7/1993
WO   WO 2005/102171 A1    3/2005

(Continued)

OTHER PUBLICATIONS

""Hovershaft": Sensorless Magnetic Bearing," Siemens Global Website (1979).

*Primary Examiner* — Michael Maskell
(74) *Attorney, Agent, or Firm* — Schiff Hardin LLP (57) ABSTRACT

A device for mounting and driving a rotatable part of a gantry of a computed tomography system with respect to a stationary part of the gantry around a system axis of the stationary part, has a magnetic bearing that magnetically supports the rotatable part relative to the stationary part, and an electromagnetic drive that drives the rotatable part of the gantry relative to the stationary part.

42 Claims, 5 Drawing Sheets

(56) References Cited

U.S. PATENT DOCUMENTS

| | | |
|---|---|---|
| 5,475,729 A | 12/1995 | Mattson et al. |
| 5,548,629 A | 8/1996 | Kimura et al. |
| 6,453,004 B1 * | 9/2002 | Albeniz et al. .................. 378/62 |
| 2005/0116558 A1 * | 6/2005 | Yokoyama et al. ......... 310/68 B |

FOREIGN PATENT DOCUMENTS

| | | |
|---|---|---|
| WO | WO 2010/026523 A2 | 3/2010 |
| WO | WO 2010026523 A2 * | 3/2010 |
| WO | WO-2010/079392 A1 | 7/2010 |

\* cited by examiner

DEVICE FOR MOUNTING AND DRIVING A ROTATABLE PART OF A GANTRY OF A COMPUTER TOMOGRAPHY UNIT AND COMPUTER TOMOGRAPHY UNIT

BACKGROUND OF THE INVENTION

1. Field of the Invention

The invention concerns a device for supporting and driving a rotatable part of a gantry of a computed tomography apparatus—which gantry has a system axis—relative to a stationary of the gantry of the computed tomography apparatus. The invention also concerns a computed tomography apparatus that embodies such a device.

2. Description of the Prior Art

Computed tomography apparatuses of the third generation have a gantry with a stationary part and a part that can be rotated relative to the stationary part. The rotatable part has the shape of a drum on which are arranged the components of the computed tomography apparatus (such as the x-ray source, the x-ray detector, a control system, etc.), which components revolve around a patient arranged along the system axis in a measurement field during operation of the computed tomography apparatus. In a system with only one x-ray source and one x-ray detector, a completely populated drum has a mass of approximately 800 kg to 900 kg and rotates with a rotation speed of up to 240 R/min during operation.

Roller bearings in different forms are presently used to support the drum relative to the stationary part of the gantry. However, the roller bearings are subject to a certain wear and must be regularly serviced (re-oiled, for example).

For example, the drive may be a motor interacting with a worm gear. Moreover, the noise level emanating from the roller bearings increases with increasing rotation speed such that it can be perceived as disruptive, and additional measures can be necessary to reduce it. The driving of the drum normally takes place via a drive belt.

SUMMARY OF THE INVENTION

An object of the invention is to provide a device and a computed tomography apparatus of the aforementioned type such that the bearing and the drive of a rotatable part of a gantry relative to a stationary part of the gantry of the computed tomography apparatus is improved.

According to the invention, this object is achieved by a device to support and drive a rotatable part of a gantry—the gantry having a system axis—of a computed tomography apparatus relative to a stationary part of the gantry of the computed tomography apparatus, having a magnetic bearing that magnetically supports the rotatable part of the gantry relative to the stationary part of the gantry, and having an electromagnetic drive that electromagnetically drives the rotatable part of the gantry relative to the stationary part of the gantry.

Due to the magnetic support of the rotatable part of the gantry relative to the stationary part of the gantry, mechanical contact no longer occurs between bearing parts. The magnetic bearing is friction-free and wear-free, such that a re-oiling or a re-greasing as with roller bearings is not necessary. With the magnetic bearing, the development of noise during operation is also markedly less than with the use of a roller bearing.

The electromagnetic drive that drives the rotatable part of the gantry relative to the stationary part of the gantry, and the magnetic bearing that supports the rotatable part of the gantry relative to the stationary part of the gantry, are advantageously combined into one unit (in particular a structural unit).

According to one variant of the invention, the magnetic bearing is formed by at least one radial magnetic bearing and at least one axial magnetic bearing.

According to a further variant of the invention, the magnetic bearing includes at least one permanent magnet, at least one electromagnet having a coil and/or at least one element made of a ferromagnetic material, and the electromagnetic drive includes at least one electromagnet having a coil. The radial and axial bearings can be realized as purely passive magnetic bearings with corresponding arrangement of permanent magnets and elements made of a ferromagnetic material on the rotatable part and the stationary part of the gantry relative to one another, making use of either the repulsive or attractive forces occurring between permanent magnets or the attractive forces between permanent magnets and ferromagnetic materials. However, to stabilize the magnetic bearings the radial and axial bearings preferably also have electromagnets that include coils in order to be able to modify the magnetic field (and therefore the currently acting forces in the respective magnetic bearings) by variation of the currents flowing through the coils of the electromagnets. For this purpose, a corresponding regulation is required that ensures that the respectively necessary bearing forces are provided.

The electromagnets (normally having multiple coils, or at least one coil) of the electromagnetic device are necessary to generate a rotating electromagnetic field to drive the rotatable part relative to the stationary part of the gantry, and for this must be controlled accordingly. The electromagnetic drive can also have permanent magnets and/or elements made of a ferromagnetic material.

According to one embodiment of the invention, the radial bearing and/or the electromagnetic drive have a first, radially outward, annular radial arrangement of permanent magnets, electromagnets and/or elements made of a ferromagnetic material that is associated with the stationary part of the gantry; and a second, radially inward, annular radial arrangement of permanent magnets, electromagnets and/or elements made of a ferromagnetic material that is associated with the rotatable part of the gantry. An annular radial bearing gap is located between the first and second annular radial arrangements.

According to a further embodiment of the invention, the at least one axial bearing has at least one first annular axial arrangement of permanent magnets, electromagnets and/or elements made of a ferromagnetic material that is associated with the stationary part of the gantry, and at least one second, annular axial arrangement of permanent magnets, electromagnets and/or elements made of a ferromagnetic material that is associated with the rotatable part of the gantry. The first and second axial arrangements are axially offset relative to one another in the direction of the tilt axis, with an annular axial bearing gap therebetween.

In a further embodiment, the device or the structural unit composed of the magnetic bearing and the electromagnetic drive has a measurement unit to determine the change of the width of the annular radial bearing gap and/or of the annular axial bearing gap. In order to be able to realize a functional and interference-free magnetic bearing, the width of the bearing gaps must be or be kept essentially constant. The width of a bearing gap is essentially the control variable in the regulation of the bearing forces. The width is preferably defined without contact with the measurement unit. The width is normally determined at at least two points of the annular bearing gap that are advantageously offset relative to one another by approximately 90°. Moreover, depending on design the width of a bearing gap does not always need to be the same over the entire bearing gap. Rather, the bearing gap can have a profile so that different widths of the bearing gap result at different points of the bearing gap. In such a case, the width of the bearing gap at a defined location of the bearing gap is respectively determined and used for regulation.

The measurement can be formed by at least one Hall sensor and/or one sensor operating inductively or capacitively.

According to a variant of the invention, if electromagnets are used for the magnetic bearing, the determination of the change of the width of the radial bearing gap and/or of the axial bearing gap takes place based on the effect of the inductivity of the coil of one or more electromagnets. For example, a position change of the inward radial arrangement of permanent magnets, electromagnets and/or elements made of a ferromagnetic material of the rotatable part of the gantry relative to the outward radial arrangement affects the inductivities of the electromagnets of the outward radial arrangement. Current and voltage values thereby change at the electromagnets of the outward radial arrangement, which changes are evaluated to determine the width of the respective bearing gap.

In an embodiment of the invention the radial bearing is arranged in a first plane, and the electromagnetic drive is arranged in a second plane that is offset relative to the first plane in the direction of the tilt axis.

In another embodiment of the invention the electromagnetic drive is integrated into the radial bearing.

According to a first variant of this embodiment, the first, radially outward, annular radial arrangement has electromagnets and the second, radially inward, radial arrangement has permanent magnets and/or elements made of a ferromagnetic material, and a group of electromagnets of the first radial arrangement is controlled such that a rotating electromagnetic field is generated to electromagnetically drive the rotatable part of the gantry.

According to a second variant of the integration embodiment, the first, radially outward, annular radial arrangement has permanent magnets and/or elements made of a ferromagnetic material and the second, radially inward, radial arrangement has electromagnets, and a group of electromagnets of the second radial arrangement is controlled such that a rotating electromagnetic field is generated to electromagnetically drive the rotatable part of the gantry.

According to a further embodiment of the invention, the first, radially outward annular radial arrangement and the second, radially inward annular arrangement have electromagnets, and a group of electromagnets of the first and/or the second radial arrangement is controlled such that a rotating electromagnetic field is generated to electromagnetically drive the rotatable part of the gantry.

According to another embodiment of the invention, the electromagnets of the first and/or the second radial arrangement that are provided for electromagnetic driving and/or for magnetic bearing are respectively grouped in segments. The electromagnets can respectively be grouped in two or more segments. For example, the electromagnets provided for electromagnetic driving can be grouped into three segments that respectively cover approximately 60° of the radial bearing; which segments are respectively separated from one another by a segment (likewise covering a 60° angle) in which are grouped electromagnets provided for magnetic bearing. Given a four-segment arrangement, the electromagnets provided for electromagnetic driving and the electromagnets provided for magnetic bearing alternately cover a respective 45° angle of the radial bearing, such that four segments are present for the driving and four segments are present for the bearing. Additional segmentations are likewise possible.

In an additional embodiment of the invention the device or the structural unit has a roller bearing as an auxiliary support bearing. In the case of a power failure, the roller bearing takes over the support function so that damage to the device is avoided.

Alternatively or additionally, an uninterruptible power supply (UPS) can be associated with the device.

The above object also is achieved in accordance with the present invention by a computed tomography apparatus having at least one device as described in the preceding.

DESCRIPTION OF THE PREFERRED EMBODIMENTS

Identical or functionally identical elements in the figures are provided with the same reference characters throughout. The representations in the figures are schematic and not necessarily true to scale. The computed tomography apparatus 1 is discussed in the following and without limitation as to generality insofar as is necessary to understand the invention.

Figure 1:
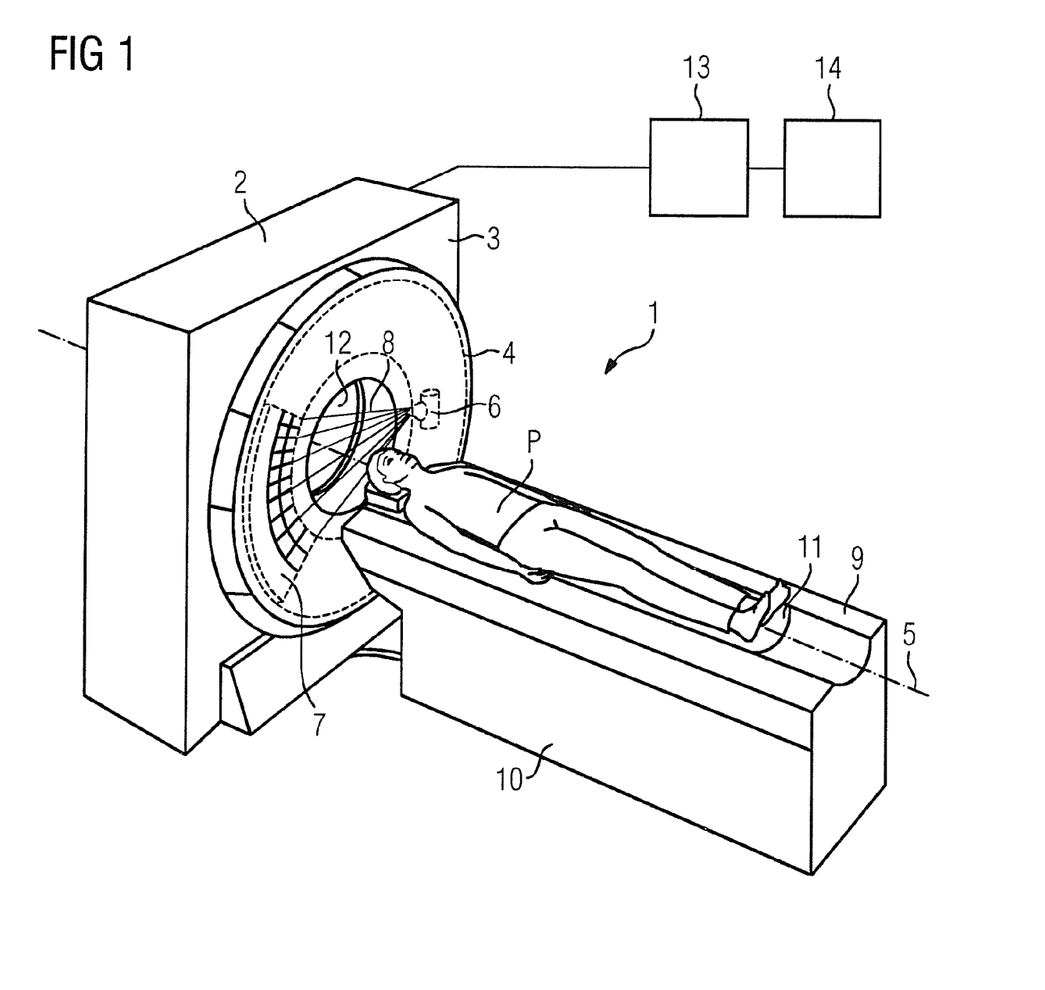
FIG. 1 schematically illustrates a computed tomography apparatus in accordance with the present invention.

The computed tomography apparatus 1 shown in FIG. 1 has a gantry 2 with a stationary part 3 and with a part 4 that can rotate around a system axis S. In the illustrated exemplary embodiment of the invention, the rotatable part 4 has an x-ray system that includes an x-ray source 6 and an x-ray detector 7 that are arranged opposite one another on the rotatable part 4. During operation of the computed tomography apparatus 1, x-ray radiation 8 emanates from the x-ray source 6 in the direction of the x-ray detector 7, penetrates a measurement subject and is detected by the x-ray detector 7 in the form of measurement data or, respectively, measurement signals.

Furthermore, the computed tomography apparatus 1 has a patient bed 9 to support a patient P to be examined. The patient bed 9 has a bed base 10 on which a patient support plate 11 is provided to actually support the patient P. The patient support plate 11 is adjustable relative to the bed base 10 in the direction of the system axis S such that it—together with the patient P—can be introduced into the opening 12 of the gantry 2 to acquire 2D x-ray projections of said patient P, for example in a spiral scan. The computational processing of the 2D x-ray projections that are acquired with the x-ray system and/or the reconstruction of slice images, 3D images or a 3D data set based on the measurement data or the measurement signals of the 2D x-ray projections takes place with an image computer 13 of the computed tomography apparatus 1, which slice images or 3D images can be presented at a display device 14.

So that the rotatable part 7 (that is provided with the x-ray system, among other things) can rotate relative to the stationary part 3 of the gantry, a rotatable bearing as well as driving of the rotatable part 4 are necessary. In the present exemplary embodiment of the invention, a bearing and drive unit 15 (schematically illustrated in FIG. 2) is provided that includes a magnetic bearing and an electromagnetic drive to effect a support and rotation of the rotatable part 4 relative to the stationary part 3 of the gantry 2. The magnetic bearing and the electromagnetic drive can in principle be formed by permanent magnets, electromagnets and/or elements made of a ferromagnetic material.

Figure 3:
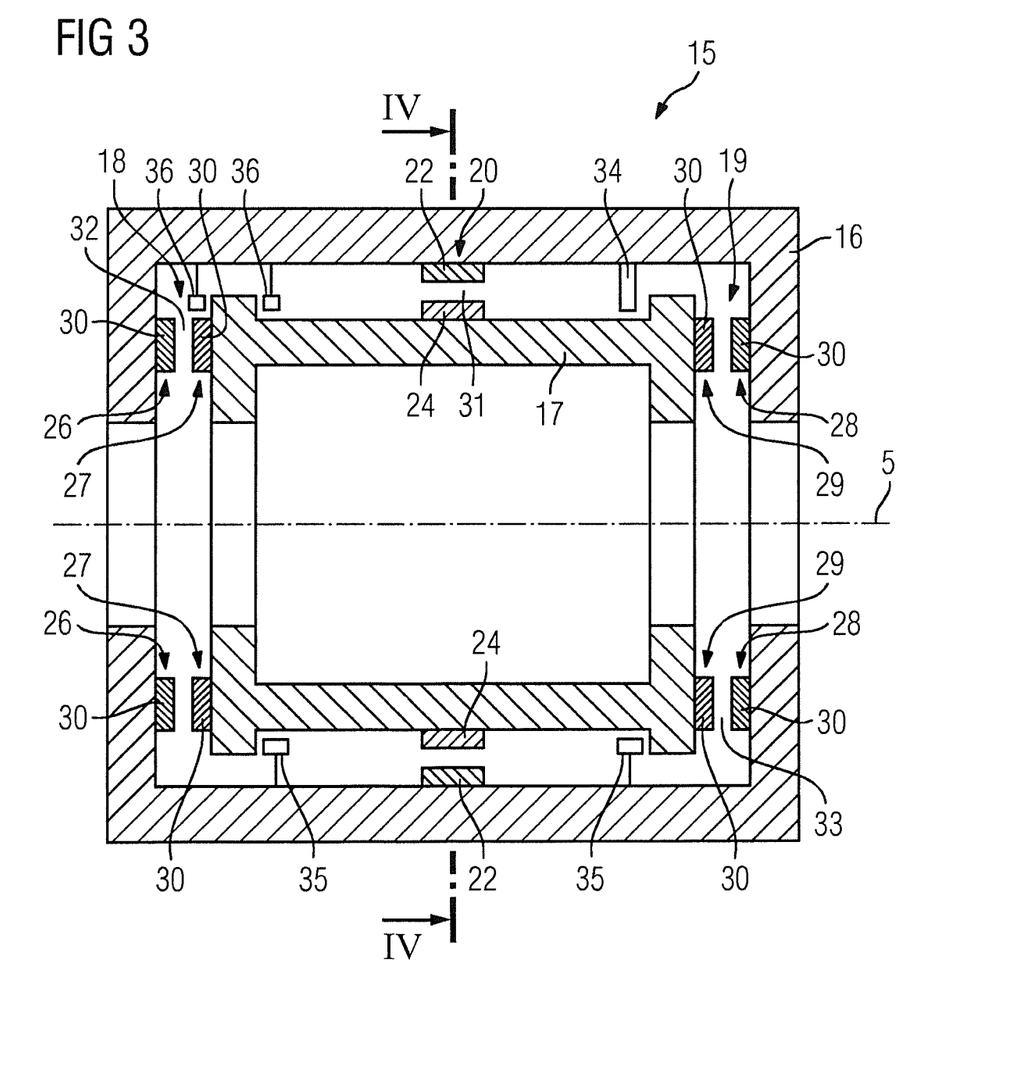
FIG. 3 is a section through a first embodiment of a bearing and drive unit according to the present invention.

FIG. 3 shows a sectional view of a first embodiment of such a bearing and drive unit 14. In the exemplary embodiment of the invention, the bearing and drive unit 15 has a first annular support element 16 arranged at the stationary part 3 and a second annular support element 17 arranged at the rotatable part 4. Components that produce the magnetic bearing and electromagnetic drive are arranged on the annular support elements 16, 17. The components in the present exemplary embodiment of the invention are two magnetic axial bearings 18, 19 and one magnetic radial bearing 20, with the electromagnetic drive integrated into the latter.

Figure 2:
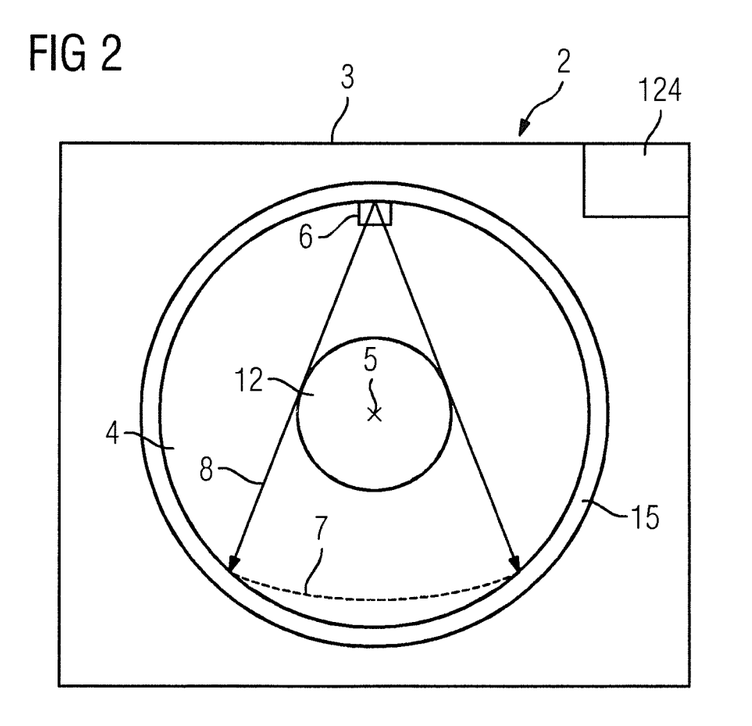
FIG. 2 schematically illustrates a stationary part and the rotatable part of the gantry of the computed tomography apparatus of FIG. 1, as well as bearing and drive unit.
Figure 4:
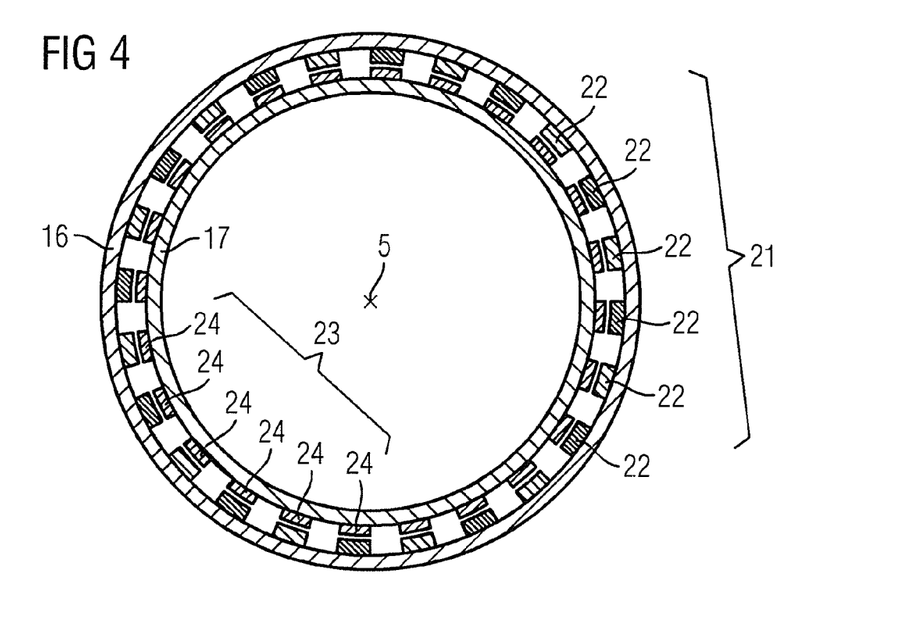
FIG. 4 is a view in the direction of arrows IV in the section of FIG. 3, in a first embodiment.

FIG. 4 shows a view of a section through the radial bearing 20 in the direction of the arrows IV from FIG. 2. In the exemplary embodiment of the invention that is shown in FIG. 4, the radial bearing 20 and electromagnetic drive that is integrated into the radial bearing 20 have a first, radially outward, annular radial arrangement 21 of electromagnets 22 which respectively comprise a coil (not explicitly shown). Furthermore, the radial bearing 20 and the electromagnetic drive that is integrated into the radial bearing 20 have a second, radially inward, annular radial arrangement 23 of elements 24 made of a ferromagnetic material. In the exemplary embodiment of the invention that is shown in FIG. 4, 50% of the electromagnets 22 serve for the magnetic bearing and 50% of the electromagnets 22 serve for the electromagnetic driving of the rotatable part 4 relative to the stationary part 3. Every other electromagnet 22 of the radially outward, annular radial arrangement 21 is provided to generate a rotating electromagnetic field, and these electromagnets 22 are controlled by a control unit (not shown) such that—by interaction with the elements 24 made of a ferromagnetic material—the rotatable part 4 is rotated relative to the stationary part 4. The remaining electromagnets 22 interact with elements 24 made of a ferromagnetic material to produce the magnetic bearing of the rotatable part 4 relative to the stationary part 3.

Instead of only the elements 24 made of a ferromagnetic material, the second radial arrangement be formed only by permanent magnets, or by both.

According to an alternative embodiment of the radial bearing 20 integrated with the electromagnetic drive, the radially outward, annular radial arrangement 21 can have elements made of a ferromagnetic material and/or permanent magnets and the radially inward, annular radial arrangement 23 can have electromagnets, wherein—as described above—every other electromagnet is provided to generate a rotating electromagnetic field in order—by interaction with the elements made of a ferromagnetic material and/or the permanent magnets—to set the rotatable part 4 into rotation relative to the stationary part 3. The remaining electromagnets, by interaction with the elements made of a ferromagnetic material and/or the permanent magnets, in turn serve for the magnetic bearing of the rotatable part 4 relative to the stationary part 3. In these variants, the electrical energy required for the generation of the rotating field and the control and regulation signals (insofar as a corresponding control and regulation unit is not arranged on the rotatable part 4) must be transmitted to the rotatable part 4 via slip rings, for example.

In an alternative embodiment of the radial bearing 20 integrated with the electromagnetic drive, both the radially outward, annular radial arrangement 21 and the radially inward, annular radial arrangement 23 have electromagnets, with at least a portion of the electromagnets of the first and second radial arrangement producing the magnetic bearing, and a group of electromagnets of the first and/or second radial arrangement is controlled such that a rotating electromagnetic field is generated to electromagnetically drive the rotatable part 4 of the gantry 2. In this case as well, the electrical energy required for the generation of the rotating field (and, if necessary, the control and regulation signals) must be transmitted to the rotatable part 4 via slip rings, for example.

Figure 5:
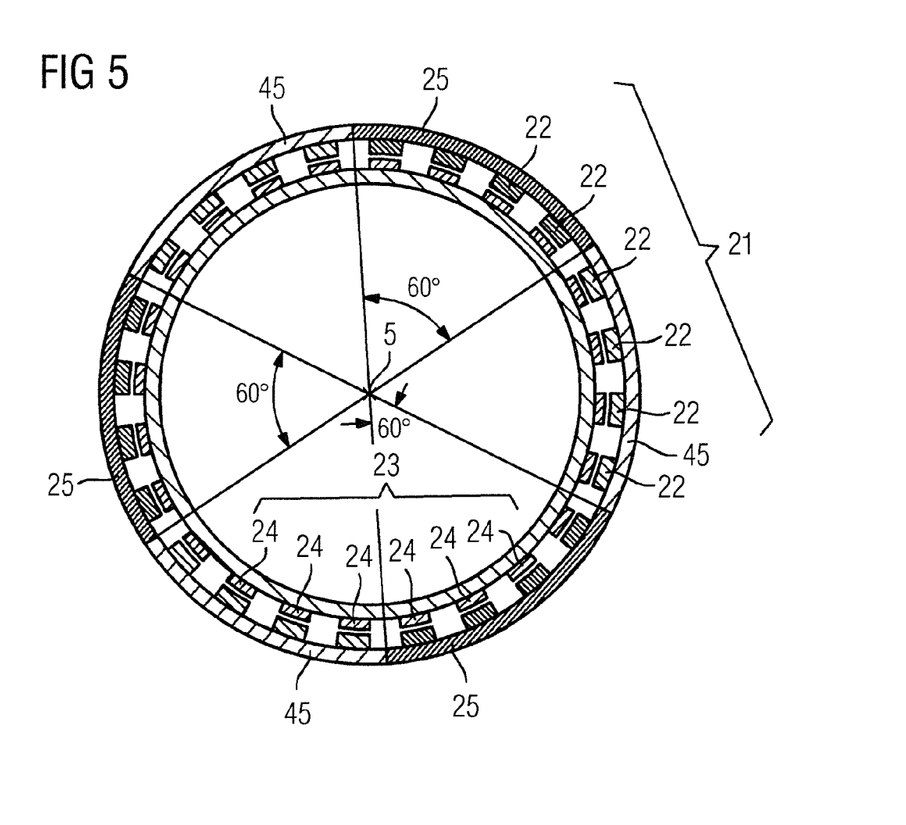
FIG. 5 is a view in the direction of arrows IV in the section of FIG. 3, in a second embodiment.

The electromagnets 22 provided for the electromagnetic driving and the electromagnets 22 of the radial bearing 20 that are provided for the magnetic bearing can also be respectively grouped into segments. FIG. 5 shows such a segmentation in a further development of the exemplary embodiment of the invention that is shown in FIG. 4. In the exemplary embodiment of the invention that is shown in FIG. 5, the electromagnets 22 provided for driving are arranged in three segments 25 that respectively cover a 60° angle, wherein a 60° angle is likewise located between each segment 25. The electromagnets 22 that are arranged in these intervening segments 45 are provided for the magnetic bearing. Other segment arrangements with other angles are likewise possible. Such a segmentation is also possible for the previously described embodiments of the radial bearing integrated with the electromagnetic drive.

In principle, the axial bearings 18 and 19 are designed like the radial bearing 20 but have no means for electromagnetic driving.

The axial bearing 18 has a first annular axial arrangement 26 of electromagnets 30 (and possibly of permanent magnets and/or of elements made of a ferromagnetic material) which are attached to the first annular support element 16 and are associated with the stationary part 3 of the gantry 2, and a second annular, axial arrangement 27 of electromagnets 30 (and possibly of permanent magnets and/or of elements made of a ferromagnetic material) which are attached to the second annular support element 17 and are associated with the rotatable part 4 of the gantry 2.

The design of the axial bearing 19 corresponds to the design of the axial bearing 18. The axial bearing 19 thus also has a first annular axial arrangement 28 of electromagnets 30 (and possibly of permanent magnets and/or of elements made of a ferromagnetic material) which are attached to the first annular support element 16 and are associated with the stationary part 3 of the gantry 2, and a second annular, axial arrangement 29 of electromagnets 30 (and possibly of permanent magnets and/or of elements made of a ferromagnetic material) which are attached to the second annular support element 17 and are associated with the rotatable part 4 of the gantry 2.

In order to be able to ensure an operation of the magnetic bearings without interference, the width of the radial bearing gap 31 and the widths of the axial bearing gaps 32 and 33 must always be determined. In the exemplary embodiment of the invention, a measurement system is provided for this in the form of Hall sensors. The width of the bearing gap does not need to be determined directly, but can be calculated from the radial or axial position of the annular support element 17 or of the rotatable part 4. If the width of a bearing gap deviates from its desired width, the width must be adjusted again to the desired width via a corresponding regulation of the coil currents of the electromagnets that are relevant to this. In the exemplary embodiment of the invention, two Hall sensors 34 (of which only one is shown in FIG. 3) arranged radially offset from one another by approximately 90° are provided to determine the width of the radial bearing gap 31. Based on the defined and known design of the bearing and drive unit 15, the width of the radial bearing gap 31 can be determined from the measurement values of the Hall sensors 34 by a control and regulation unit and be used to control and regulate the coil currents of the electromagnets relevant to the radial bearing.

The widths of the axial bearing gaps 32 and 33 are determined in a corresponding manner. A first arrangement of Hall sensors 35 and a second arrangement of Hall sensors 36 are shown in FIG. 3. At least two first arrangements of Hall sensors 35 and/or at least two second arrangements of Hall sensors 36, radially offset relative to one another by approximately 90° relative to one another, are preferably present to acquire measurement values. The width of the axial bearing gap 32 and the width of the axial bearing gap 33 can be determined by a control and regulation unit from the measurement values of the Hall sensors 35 and/or of the Hall sensors 36 and be used for control and regulation of the coil currents of the electromagnets relevant to the axial bearing.

Alternatively, the determination of the widths of the bearing gaps 31 through 33 can be implemented with additional sensors with evaluation only of the changes of current and voltage values of electromagnets. The inductivities of the electromagnets relevant to the magnetic bearing are influenced as a result of a position change of the annular support element 17 or of the rotatable part 4 relative to the annular support element 16 or the stationary part 3, thereby causing the current and voltage values at the relevant electromagnets to change. The widths of the bearing gaps can respectively be determined by the evaluation of these current and voltage values and be used for the control and regulation of the coil currents of the relative electromagnets.

Figure 6:
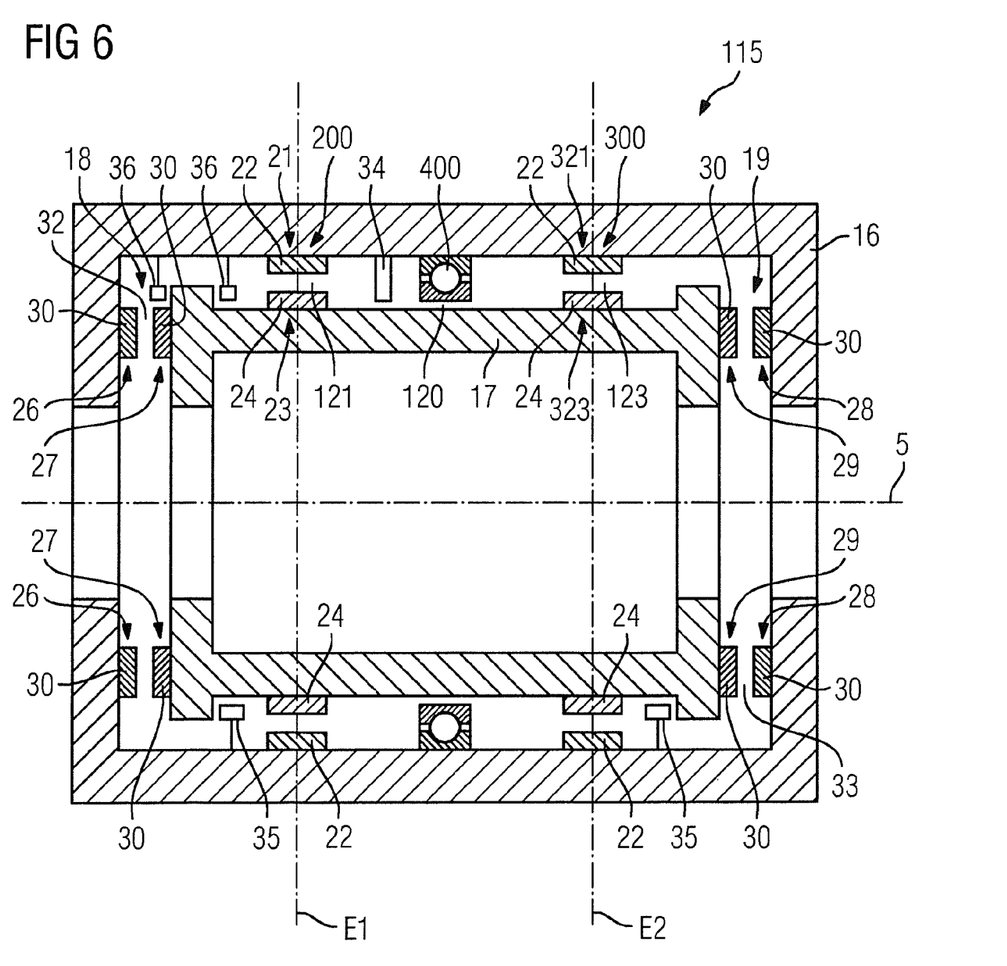
FIG. 6 is a section through a further embodiment of a bearing and drive unit according to the present invention.

Hall sensors can moreover also be used for rotation monitoring, wherein a Hall sensor can be used in order to detect the rotation position of the annular support element 17 relative to the annular support element 16. One or two additional Hall sensors can be provided in order to detect the rotation direction. These sensors are also preferably integrated into the bearing and drive unit 15. FIG 6 shows a section representation of a second exemplary embodiment of a bearing and drive unit 115 which differs from the bearing and drive unit 15 in that the radial bearing 200 and the electromagnetic drive unit 300 are separate from one another and are arranged offset relative to one another in the direction of the axis 5. Moreover, the bearing and drive unit 115 has a support bearing 400. The remaining components of the bearing and drive unit 115 correspond in design and function, as necessary with dimensions adapted to the structural shape of said bearing and drive unit 215, to the components of the bearing and drive unit 15, which is why these are provided with the same reference characters.

In the exemplary embodiment of the invention that is shown in FIG. 6, the radial bearing 200 is arranged in a first plane E1 and—like the radial bearing 20 integrated with the electromagnetic drive—has a radially outward, annular radial arrangement 21 and a radially inward, annular radial arrangement 23 of electromagnets, and possibly of permanent magnets and/or elements made of a ferromagnetic material.

The electromagnetic drive unit 300 is arranged in a plane E2, offset relative to the plane E1 in the direction of the system axis 5, and likewise has a radially outward, annular radial arrangement 321 and a radially inward, annular radial arrangement 323 of electromagnets, and possibly of permanent magnets and/or elements made of a ferromagnetic material.

In contrast to the radial bearing 20 integrated with the electromagnetic drive, all electromagnets 22 (and if applicable permanent magnets and/or elements made of a ferromagnetic material) of the radial bearing 200 are provided for the magnetic bearing. Furthermore, all electromagnets (and if applicable permanent magnets and/or elements made of a ferromagnetic material) of the electromagnetic drive unit 300 are provided for electromagnetic driving.

As noted, in addition to this the bearing and drive unit 115 also has a support bearing 400 in the form of a conventional roller bearing. The support bearing 400 takes over the support function in the bearing and drive unit 115 if the magnetic field generated by the electromagnets becomes too weak (for example in the event of a power failure). Damage to the magnet bearing of the bearing and drive unit 115 is also avoided in this way. In order to fulfill this purpose, the width of the column 120 between the support bearing 400 arranged at the support el 16 and the support el 17 is smaller than the radial bearing gap 121 and smaller than the drive gap 123. In normal operation, the support bearing 400 attached to the annular support element 16 does not contact the annular support element 17. Only in the event of an error does the support bearing 400 contact the annular support element 17 and take over the support function, whereby a damage to the radial bearing 200 and the electromagnetic drive unit 300 is avoided.

Additionally or alternatively, the device or the computed tomography apparatus can have an uninterruptible power supply 124 as this is indicated in FIG. 2. As is shown for the bearing and drive unit 15, a support bearing is not necessary since the power and voltage supply is ensured by the uninterruptible power supply 124 in the event of a power outage.

Although modifications and changes may be suggested by those skilled in the art, it is the intention of the inventors to embody within the patent warranted heron all changes and modifications as reasonably and properly come within the scope of their contribution to the art.

We claim as our invention:

1. A device to support and drive a rotatable part of a gantry of a computed tomography apparatus relative to a stationary part of said gantry, said gantry comprising a system axis and said rotatable part and said stationary part having an annular gap therebetween that proceeds around said system axis, said device comprising:

a magnetic radial bearing configured to magnetically support said rotatable part of said gantry radially with respect to said system axis, relative to said stationary part of said gantry;

an electromagnetic drive configured to rotate said rotatable part of said gantry around said system axis relative to said stationary part of said gantry;

a plurality of magnetic components, said plurality extending completely around said system axis in said annular gap, with all of said magnetic components situated in a plane that is perpendicular to said system axis;

said magnetic radial bearing comprising a first sub-plurality of said plurality of magnetic components and said electromagnetic drive comprising a second sub-plurality of said plurality of magnetic components, with no magnetic component in said plurality of magnetic components being in both said first sub-plurality and in said second sub-plurality; and the magnetic components in said first sub-plurality alternating around said annular gap in said plane with the magnetic components in said second sub-plurality.

2. A device as claimed in claim 1 comprising at least one magnetic axial bearing that support said rotatable part with respect to a plane that is perpendicular to said system axis.

3. A device as claimed in claim 1 wherein said first sub-plurality comprises magnetic components selected from the group consisting of permanent magnets, electromagnets, and elements composed of ferromagnetic material, and wherein all magnetic components in said second sub-plurality are electromagnets.

4. A device as claimed in claim 1 wherein each pf said first sub-plurality of magnetic components of said radial bearing and said second sub-plurality of magnetic components of said electromagnetic drive is comprised of a first, radially outlying annular radial arrangement of magnetic components that are mechanically associated with said stationary part of said gantry, and a second, radially inward, annular radial arrangement of magnetic components that are mechanically associated with said rotatable part of said gantry, and wherein an annular radial gap exists between said first and second annular radial arrangements.

5. A device as claimed in claim 4 comprising a measurement unit configured to determine a change of a width of said annular radial separation.

6. A device as claimed in claim 5 wherein said measurement unit comprises at least one measurement component selected from the group consisting of Hall sensors, inductive sensors, and capacitive sensors.

7. A device as claimed in claim 5 wherein said magnetic components in said first sub-plurality of said magnetic radial bearing are individual electromagnets, each having a coil exhibiting an inductance, and wherein said measurement unit comprises a component configured to determine said change of said width of said annular radial separation by detecting a change in the inductance of at least one of the respective coils of said plurality of electromagnets.

8. A device as claimed in claim 2 wherein said magnetic axial bearing is comprised of a first axial arrangement of components selected from the group consisting of permanent magnets, electromagnets, and elements composed of ferromagnetic material, said first axial arrangement being mechanically associated with said stationary part of said gantry, and a second, axial arrangement that is axially spaced from said first axial arrangement along said system axis and that is comprised of components selected from the group consisting of permanent magnets, electromagnets, and elements composed of ferromagnetic material, said second axial arrangement being mechanically associated with said rotatable part of said gantry, and wherein an annular axial separation exists between said first and second axial arrangements.

9. A device as claimed in claim 8 comprising a measurement unit configured to determine a change of a width of said annular axial separation.

10. A device as claimed in claim 9 wherein said measurement unit comprises at least one measurement component selected from the group consisting of Hall sensors, inductive sensors, and capacitive sensors.

11. A device as claimed in claim 9 wherein said magnetic axial bearing comprises a plurality of electromagnets, each having a coil exhibiting an inductance, and wherein said measurement unit comprises a component configured to determine said change of said width of said annular axial separation by detecting a change in the inductance of at least one of the respective coils of said plurality of electromagnets.

12. A device as claimed in claim 1 wherein each of said first sub-plurality of magnetic components of said magnetic radial bearing and said second sub-plurality of magnetic components of said electromagnetic drive comprises a first, radially outward, annular radial arrangement of magnetic components selected from the group consisting of permanent magnets and elements composed of ferromagnetic material, mechanically associated with said stationary part, and a second, radially inward, annular radial arrangement of electromagnets mechanically associated with said rotatable part, and wherein said device comprises a control computer configured to operate said electromagnets to produce a rotating electromagnetic field that rotates around said stationary part to electromagnetically rotate said rotatable part of said gantry relative to said stationary part of said gantry.

13. A device as claimed in claim 12 wherein said electromagnets are divided into groups respectively forming segments of a circle around said stationary part, and wherein said control computer is configured to control the respective groups of electromagnets to produce said rotating electromagnetic field.

14. A device as claimed in claim 1 wherein each of said first sub-plurality of magnetic components of said magnetic radial bearing and said second sub-plurality of magnetic components of said electromagnetic drive comprises a first, radially outward, annular radial arrangement of electromagnets mechanically associated with said stationary part, and a second, radially inward, annular radial arrangement of electromagnets mechanically associated with said rotatable part, and wherein said device comprises a control computer configured to operate said electromagnets to produce a rotating electromagnetic field that rotates around said stationary part to electromagnetically rotate said rotatable part of said gantry relative to said stationary part of said gantry.

15. A device as claimed in claim 14 wherein said electromagnets are divided into groups respectively forming segments of a circle around said stationary part, and wherein said control computer is configured to control the respective groups of electromagnets to produce said rotating electromagnetic field.

16. A device as claimed in claim 1 comprising a roller bearing that mechanically supports said rotatable part relative to said stationary part.

17. A device as claimed in claim 1 comprising an uninterruptable power supply that supplies power at least to said electromagnetic drive.

18. A computed tomography apparatus comprising:
a gantry comprising a stationary part and a rotatable part that is rotatable relative to said stationary part, said gantry having a system axis around which said rotation of said rotatable part occurs, with said stationary part and said rotatable part having an annular gap therebetween that proceeds around said system axis;
an x-ray radiator and an x-ray radiation detector mounted on said rotatable part on opposite sides of said system axis in said plane;
a magnetic radial bearing configured to magnetically support said rotatable part of said gantry relative to said stationary part of said gantry;
an electromagnetic drive configured to rotate said rotatable part of said gantry around said system axis relative to said stationary part of said gantry;
a plurality of magnetic components, said plurality extending completely around said system axis in said annular gap, with all of said magnetic components situated in a plane that is perpendicular to said system axis;

said magnetic radial bearing comprising a first sub-plurality of said plurality of magnetic components and said electromagnetic drive comprising a second sub-plurality of said plurality of magnetic components, with no magnetic component in said plurality of magnetic components being in both said first sub-plurality and in said second sub-plurality;

the magnetic components in said first sub-plurality alternating around said annular gap in said plane with the magnetic components in said second sub-plurality; and a control computer configured to operate said x-ray radiator and said x-ray radiation detector to acquire computed tomography data while said rotatable part is rotating around said stationary part.

19. A device as claimed in claim 1 comprising at least one magnetic axial bearing that support said rotatable part with respect to a plane that is perpendicular to said system axis.

20. A computed tomography apparatus as claimed in claim 18 wherein said first sub-plurality comprises magnetic components selected from the group consisting of permanent magnets, electromagnets, and elements composed of ferromagnetic material, and wherein all magnetic components in said second sub-plurality are electromagnets.

21. A computed tomography apparatus as claimed in claim 18 each pf said first sub-plurality of magnetic components of said radial bearing and said second sub-plurality of magnetic components of said electromagnetic drive is comprised of a first, radially outlying annular radial arrangement of magnetic components that are mechanically associated with said stationary part of said gantry, and a second, radially inward, annular radial arrangement of magnetic components that are mechanically associated with said rotatable part of said gantry, and wherein an annular radial gap exists between said first and second annular radial arrangements.

22. A computed tomography apparatus as claimed in claim 21 comprising a measurement unit configured to determine a change of a width of said annular radial separation.

23. A computed tomography apparatus as claimed in claim 22 wherein said measurement unit comprises at least one measurement component selected from the group consisting of Hall sensors, inductive sensors, and capacitive sensors.

24. A computed tomography apparatus as claimed in claim 22 wherein said magnetic components in said first sub-plurality of said magnetic radial bearing are individual electromagnets, each having a coil exhibiting an inductance, and wherein said measurement unit comprises a component configured to determine said change of said width of said annular radial separation by detecting a change in the inductance of at least one of the respective coils of said plurality of electromagnets.

25. A computed tomography apparatus as claimed in claim 19 wherein said magnetic axial bearing is comprised of a first axial arrangement of components selected from the group consisting of permanent magnets, electromagnets, and elements composed of ferromagnetic material, said first axial arrangement being mechanically associated with said stationary part of said gantry, and a second, axial arrangement that is axially spaced from said first axial arrangement along said system axis and that is comprised of components selected from the group consisting of permanent magnets, electromagnets, and elements composed of ferromagnetic material, said second axial arrangement being mechanically associated with said rotatable part of said gantry, and wherein an annular axial separation exists between said first and second axial arrangements.

26. A computed tomography apparatus as claimed in claim 25 comprising a measurement unit configured to determine a change of a width of said annular axial separation.

27. A computed tomography apparatus as claimed in claim 26 wherein said measurement unit comprises at least one measurement component selected from the group consisting of Hall sensors, inductive sensors, and capacitive sensors.

28. A computed tomography apparatus as claimed in claim 25 wherein said magnetic axial bearing comprises a plurality of electromagnets, each having a coil exhibiting an inductance, and wherein said measurement unit comprises a component configured to determine said change of said width of said annular axial separation by detecting a change in the inductance of at least one of the respective coils of said plurality of electromagnets.

29. A computed tomography apparatus as claimed in claim 18 wherein each of said first sub-plurality of magnetic components of said magnetic radial bearing and said second sub-plurality of magnetic components of said electromagnetic drive comprises a first, radially outward, annular radial arrangement of magnetic components selected from the group consisting of permanent magnets and elements composed of ferromagnetic material, mechanically associated with said stationary part, and a second, radially inward, annular radial arrangement of electromagnets mechanically associated with said rotatable part, and wherein said control computer is configured to operate said electromagnets to produce a rotating electromagnetic field that rotates around said stationary part to electromagnetically rotate said rotatable part of said gantry relative to said stationary part of said gantry.

30. A computed tomography apparatus as claimed in claim 29 wherein said electromagnets are divided into groups respectively forming segments of a circle around said stationary part, and wherein said control computer is configured to control the respective groups of electromagnets to produce said rotating electromagnetic field.

31. A computed tomography apparatus as claimed in claim 18 wherein each of said first sub-plurality of magnetic components of said magnetic radial bearing and said second sub-plurality of magnetic components of said electromagnetic drive comprises a first, radially outward, annular radial arrangement of electromagnets mechanically associated with said stationary part, and a second, radially inward, annular radial arrangement of electromagnets mechanically associated with said rotatable part, and wherein said control computer is configured to operate said electromagnets to produce a rotating electromagnetic field that rotates around said stationary part to electromagnetically rotate said rotatable part of said gantry relative to said stationary part of said gantry.

32. A computed tomography apparatus as claimed in claim 31 wherein said electromagnets are divided into groups respectively forming segments of a circle around said stationary part, and wherein said control computer is configured to control the respective groups of electromagnets to produce said rotating electromagnetic field.

33. A computed tomography apparatus as claimed in claim 18 comprising a roller bearing that mechanically supports said rotatable part relative to said stationary part.

34. A computed tomography apparatus as claimed in claim 18 comprising an uninterruptable power supply that supplies power at least to said electromagnetic drive.

35. A device as claimed in claim 1 wherein the magnetic components in said first sub-plurality alternate around said annular gap in said plane with the magnetic components in said second sub-plurality with every magnetic component in said first sub-plurality being between two magnetic components in said second sub-plurality and every magnetic component in said second sub-plurality being between two magnetic components in said first sub-plurality.

36. A device as claimed in claim 1 wherein said magnetic components in said first sub-plurality alternate in angular sectors in said plane around said system axis with magnetic components in different angular sectors in said second sub-plurality, with each angular sector comprising only magnetic components in said first sub-plurality or only magnetic components in said second sub-plurality.

37. A device as claimed in claim 36 wherein each angular sector encompasses 60° of said annular gap in said plane.

38. A device as claimed in claim 36 wherein each angular sector encompasses 45° of said annular gap in said plane.

39. A computed tomography apparatus as claimed in claim 18 wherein the magnetic components in said first sub-plurality alternate around said annular gap in said plane with the magnetic components in said second sub-plurality with every magnetic component in said first sub-plurality being between two magnetic components in said second sub-plurality and every magnetic component in said second sub-plurality being between two magnetic components in said first sub-plurality.

40. A computed tomography apparatus as claimed in claim 18 wherein said magnetic components in said first sub-plurality alternate in angular sectors in said plane around said system axis with magnetic components in different angular sectors in said second sub-plurality, with each angular sector comprising only magnetic components in said first sub-plurality or only magnetic components in said second sub-plurality.

41. A computed tomography apparatus as claimed in claim 40 wherein each angular sector encompasses 60° of said annular gap in said plane.

42. A computed tomography apparatus as claimed in claim 40 wherein each angular sector encompasses 45° of said annular gap in said plane.

* * * * *